United States Patent [19]

Ligon, Jr.

[11] 4,004,881
[45] Jan. 25, 1977

[54] APPARATUS FOR GENERATING CARRIER GAS-TEST SPECIMEN VAPOR MIXTURES FOR DELIVERY INTO A GAS CHROMATOGRAPH

[75] Inventor: Woodfin V. Ligon, Jr., Schenectady, N.Y.

[73] Assignee: General Electric Company, Schenectady, N.Y.

[22] Filed: Dec. 18, 1975

[21] Appl. No.: 641,837

[52] U.S. Cl. .......................... 23/232 C; 23/253 PC; 73/23.1
[51] Int. Cl.² .................. G01N 31/08; G01N 31/12
[58] Field of Search ..... 23/232 C, 253 PC, 230 PC; 73/23.1

[56] References Cited
UNITED STATES PATENTS

| | | |
|---|---|---|
| 3,063,286 | 11/1962 | Nerheim .............................. 73/23.1 |
| 3,304,159 | 2/1967 | Hinsvark .......................... 23/232 C |
| 3,374,660 | 3/1968 | McKinney et al. .............. 23/232 C |
| 3,498,107 | 3/1970 | Kim et al. .......................... 73/23.1 |
| 3,647,385 | 3/1972 | Stephens ................... 23/253 PC X |

*Primary Examiner*—Robert M Reese
*Attorney, Agent, or Firm*—Charles T. Watts; Joseph T. Cohen; Jerome C. Squillaro

[57] ABSTRACT

Delivery of a test specimen vapor—carrier gas mixture into a gas chromatograph is accomplished by means of an apparatus including a barrel to receive a probe which serves to maintain the test specimen in contact with carrier gas within the barrel, a heating coil disposed around portions of the barrel housing the sample, and a compression seal releasably bearing against a portion of the probe to prevent air flow into and gas flow from the open end of the barrel.

4 Claims, 4 Drawing Figures

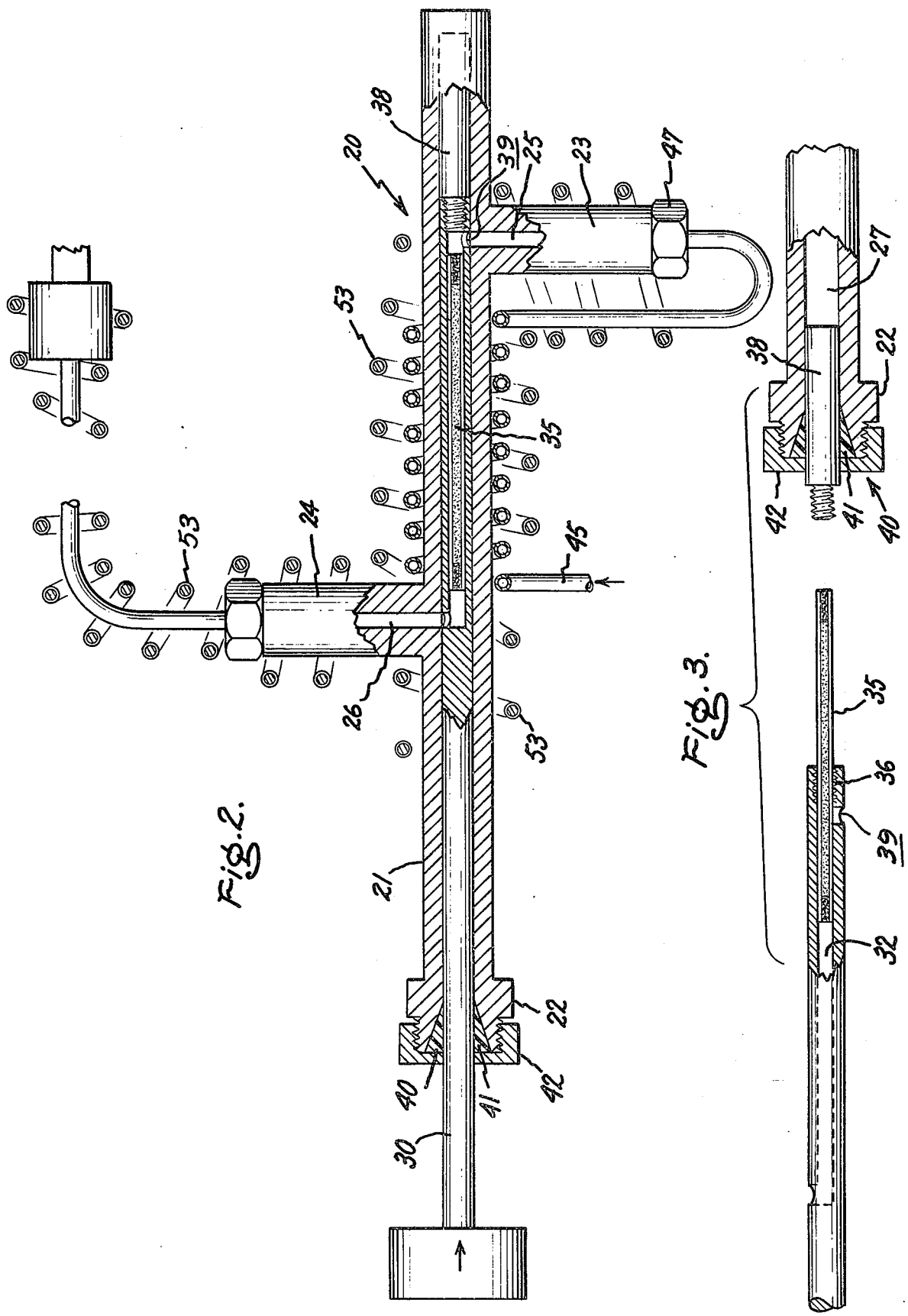

APPARATUS FOR GENERATING CARRIER GAS-TEST SPECIMEN VAPOR MIXTURES FOR DELIVERY INTO A GAS CHROMATOGRAPH

The present invention relates generally to the art of gas analysis and is more particularly concerned with novel apparatus for generation of test specimen vapor—carrier gas mixtures and for the delivery of them free of air contamination and in comparatively rapid sequence into the column of a gas chromatographic instrument.

BACKGROUND OF THE INVENTION

Identification and monitoring of organic compounds in the parts per million range in industrial atmospheres, for example, commonly involves adsorbent techniques and gas chromatography. Organics are removed from adsorbents such as charcoal, porous polymers or the like either by solvent extraction or preferably by evaporation when thermal stability permits. Because adsorbed test samples often do not consist of a single material and even after adsorbent concentration are still in the submilligram range, gas chromatography is used to make the necessary separation. Positive identification of the resulting gas chromatographic peaks is normally made through the use of a directly coupled mass spectrometer.

In the best prior art practice, a sample tube containing an adsorbed sample is coupled into a carrier gas loop external to the gas chromatograph—mass spectrometer assembly and heated in a suitable oven to accomplish quantitative transfer of the adsorbed organic material of interest to the head of the gas chromatographic column. This procedure involves certain substantial difficulties, however, including the exclusion of air, which is an essential requirement of any mass spectrometry operation. In addition, such installation and removal of the sample tubes in the system is time-consuming, as is the oven heating and cooling cycle, and the sealing problem is aggravated by the necessity for frequently opening and closing the external carrier gas loop as sample tubes are coupled and uncoupled in it.

SUMMARY OF THE INVENTION

The foregoing shortcomings can be avoided and new advantages and results can be obtained through the application of my novel concepts to be described. In particular, both the external oven and the heating—cooling cycle time requirement can be eliminated. Additionally, by virtue of the elimination in this new design of the troublesome sample tube seals, the sample tube can be coupled and uncoupled in the carrier gas system more readily and quickly and the problem of air contamination of the instruments is eliminated for all practical purposes. Still further, all these features are available without incurring any offsetting disadvantage of economy or penalty of performance of the associated instrument system.

One of these new concepts of mine is to provide means for functionally incorporating the sample tube temporarily into a carrier gas line without mechanically joining it to the line. Another of my new concepts is to provide such means in the general form of a barrel-like vessel open only at one end to receive a probe to support a sample tube within the vessel at a location where the carrier gas stream is flowing during operation of the equipment. Further, the vessel has carrier gas inlet and outlet openings for axial flow of carrier gas through the vessel and through the sample tube in contact with the adsorbed specimen. The carrier gas supply line and a conduit for receiving carrier gas—test specimen vapor mixtures in the outlet opening of the vessel are heated along with the vessel and the adsorbed sample therein by an electrical resistance heating coil disposed around the vessel, the inlet line and the conduit. The sealing of the vessel during sample evaporation or desorption and during loading is accomplished by means of a single compression fitting which in cooperation with the probe gas-tightly closes the open end of the vessel. Finally, the vessel, together with the probe, the line and the conduit and the heating coil is provided as an assembly which is detachably mountable on a gas chromatograph housing for operational connection to the column of the instrument.

DESCRIPTION OF THE DRAWINGS

FIG. 2 is an enlarged side elevational view of the apparatus of this invention as shown in FIG. 1, parts being broken away for clarity;

FIG. 3 is an exploded view of portions of the probe and vessel with the sample tube partially contained in the probe as during loading or unloading of the apparatus.

DETAILED DESCRIPTION OF THE INVENTION

Figure 1:
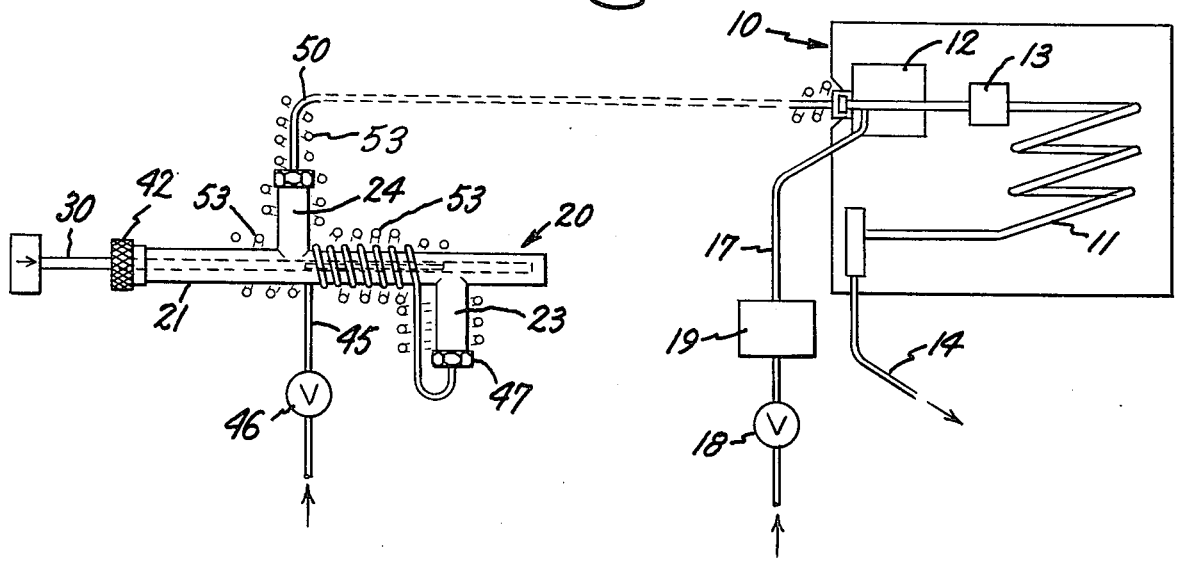
FIG. 1 is a diagrammatic view of a gas chromatographic assembly including the apparatus of this invention in preferred form.

As shown in FIG. 1, gas chromatograph 10 comprising column 11 and the usual associated parts of the instrument including injector 12 and sample collector 13, is connected to a mass spectrometer (not shown) by line 14 and additionally is connected to a source of helium carrier gas through line 17 equipped with valve 18 and pressure regulator 19. Apparatus 20 of this invention is shown operatively coupled to column 11. As indicated above, apparatus 20 is preferably furnished in a form adaptable to mounting on the housing of instrument 10.

Apparatus 20 comprises a barrel-like body 21 having an open end 22 and projections 23 and 24 having central bores 25 and 26, respectively, communicating with an axial bore 27 (FIG. 3) and thus providing a carrier gas inlet port or passageway and a gas—vapor mixture outlet port or passageway for the barrel. Probe 30 has an elongated body portion of diameter approximating the diameter of axial bore 27 and has an axial bore 32 in which to receive the sample tube 35 as shown to best advantage in FIG. 3. The inner end of the probe is provided with internal threads 36 for attachment to blank-off plug 38. A carrier gas inlet opening 39 and a gas—vapor mixture outlet opening are provided in probe 30 near the ends of bore 32.

A ferruled compression fitting assembly 40 including Teflon seal 41 and cap 42 serves to gas-tightly close open end 22 of barrel 21 around an annular portion of either probe 30, as shown in FIG. 2, or blank-off plug 38, as shown in FIG. 3, threads being provided on the projection of barrel 21 for easy attachment and removal of the internally-threaded cap.

An auxiliary source of helium carrier gas is provided through carrier gas inlet or supply line 45, flow being regulated by means of a suitable valve 46. As illustrated in FIG. 1, line 45 is coiled around barrel 21 between projections 23 and 24, terminating in a fitting 47 secured to projection 23 to seal against leakage of helium from the system as the carrier gas is delivered into and flowed through barrel 21.

A gas conduit 50 is similarly connected to the end of projection 24 of the vessel to receive carrier gas—specimen vapor mixtures and to conduct them to column 11 of instrument 10 as shown in FIG. 1.

An electrical resistance heating coil 53 is disposed around barrel 21 and the coil portion of inlet line 45 and is also disposed around projections 23 and 24 as well as conduit 50 between projection 24 and instrument 10. Thus, electrical resistance heating is established and maintained during operation, and the sample tube and its contents as well as the adjoining portions of the barrel are maintained at the desired operating temperature level until the sample has been quantitatively transferred to gas chromatograph column 11.

Figure 4:
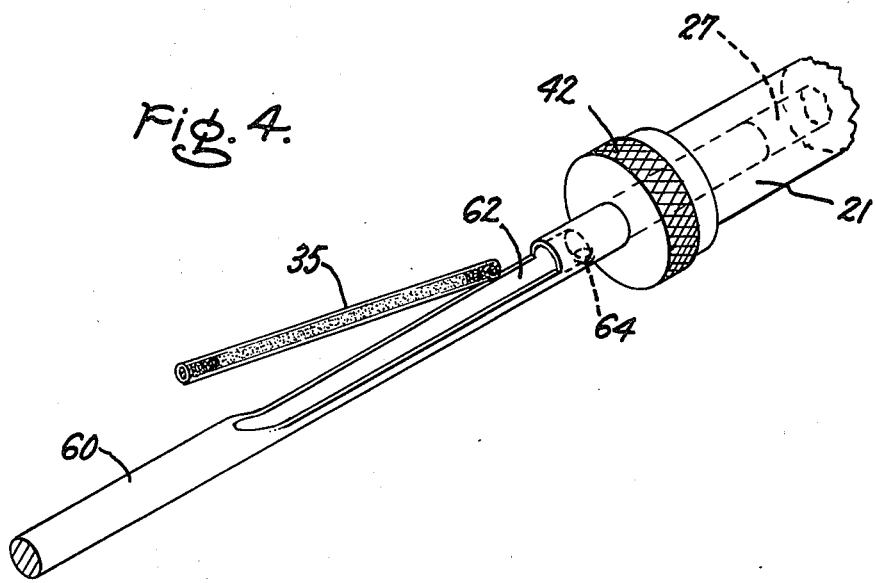
FIG. 4 is a fragmentary perspective view of another probe of this invention shown in loading or unloading position, the open-ended vessel being closed around the shank of the probe.

The alternative probe design of this invention shown in FIG. 4 differs from that of FIG. 3 in that the blank-off plug has been eliminated. Additionally, the probe has an axially-extending recess open over most of its length to facilitate introduction and removal of the sample tubes. Specifically, probe 60 is sized for close fitting receipt in barrel 21 and has an axial recess 62 of length slightly longer than sample tube 35. A portion of the length of the probe in the region of recess 62 is cut away to facilitate loading and unloading of the probe. Carrier gas inlet opening 64 is provided near one end of recess 62 for delivery of carrier gas from inlet line 45 into barrel 21 and into the leading end of sample tube 35. Thus, the leading end of tube 35 is received in close fitting engagement with probe 60 in the portion adjoining inlet opening 64 so that carrier gas is caused to flow in large part through tube 35. Carrier gas flowing from the trailing end of tube 35 emerges into the limited space between tube 35 and barrel 21 where probe 60 is cut away to provide the sample tube loading slot. Carrier gas in that relatively small axially-extending space is forced through bore 26 and conduit 50 and ultimately is introduced into injector 12 of chromatograph 10 as described in detail in reference to FIG. 2.

From the foregoing description it will be understood by those skilled in the art that the illustrated apparatus of this invention can readily be constructed as a self-contained unit for attachment to the gas chromatograph. It will be further understood that in use with such an instrument or with such an instrument in combination with a mass spectrometer, as indicated in FIG. 1, the analytical equipment will be operated in generally the usual way, carrier gas flowing into column 11 from conduit 50 while the sample is being desorbed in barrel 21 and carrier gas being delivered into column 11 from line 17 after the sample has been quantitatively transferred to collection point 13 which consists of an externally cooled part of column 11.

With the illustrated apparatus coupled to instrument 10, one may proceed with the test operation by releasing compression fitting 40, withdrawing probe 30 from barrel 21, securing fitting 40 on the blank-off plug, disengaging the probe from the plug and inserting sample tube 35 into central bore 32. Then, with the probe and blank-off plug again joined together and the sample tube within the probe, the compression seal is released and the probe and plug are moved together into the position illustrated in FIG. 2 and the compression seal is then again reestablished around an annular portion of the probe disposed within the seal section.

As indicated above, valve 46 is open and valve 18 is closed until the sample in tube 35 has been transferred completely to externally cooled collection point 13 of instrument 10. Then valve 46 is closed and valve 18 is opened for delivery of carrier gas via regulator 19 to instrument 10, the sample being picked up at collection point 13 and moved down column 11 by the regulated carrier gas flow. External cooling of collection area 13 is stopped at this point and the column 11 is temperature programmed. At the conclusion of this analysis stage, valve 18 is closed and valve 46 is opened, whereupon the exhausted sample tube can be replaced with a fresh one.

Heating of barrel 21 is preferably continuous throughout the period of use of the instrument with a series of test samples. Thus, at the outset a switch (not shown) controlling an electric circuit (also not shown) providing power to coil 53 is closed and the heating is begun. Preferably, the switch is a potentiometer calibrated to deliver power required to establish and maintain the temperature desired within sample tube 35 to accomplish complete desorption or vaporization of the specimen material to be analyzed in the associated instruments in only a minute or two. Gas flow through line 45 is adjusted preferably to insure that specimen vapors will be swept into conduit 50 and instrument 10 at a rate which is limited only by the capacity of column 11 of the instrument. When the sample has thus been removed from the sample tube, sample tube 35 is removed for replacement immediately by the next in the series by repeating the steps described above.

Operation of the apparatus illustrated in FIG. 4 is basically the same except that the step of disengaging the probe from the blank-off plug is eliminated, the probe serving both the loading and the operating sealing functions, and the sample tube is side loaded instead of end loaded and is similarly removed, as the drawing illustrates.

What I claim as new and desire to secure by Letters Patent of the United States is:

1. In a gas chromatograph instrument including a hollow coil gas chromatographic column having an inlet end to receive a mixture of carrier gas and test specimen vapor and an outlet end adapted for connection to a mass spectrometer, the combination of specimen vapor generation and delivery apparatus comprising as an assembly:
   a. a barrel open at one end to receive a specimen to be vaporized and delivered quantitatively into the gas chromatographic column and having carrier gas inlet and outlet opening axially spaced for carrier gas flow through the barrel in contact with a specimen contained therein,
   b. a carrier gas conduit connected to the inlet end of the said column and to the barrel and communicating with the barrel gas outlet opening to receive carrier gas and specimen vapor mixtures for delivery into the said column,
   c. a carrier gas supply line connected to the barrel and communicating with the carrier gas inlet opening of the barrel,
   d. an elongated cylindrical probe slidable axially in the barrel having a specimen-receiving chamber and axially spaced carrier gas inlet and outlet openings for registry respectively with the barrel inlet and outlet openings, e. barrel closure means secured to the open end of the barrel including a releasable seal cooperating with the probe to close the barrel open end against gas flow while carrier gas is flowing in contact with a test specimen in the barrel, and f. heating means comprising an electrical resistance heating coil disposed around the barrel between the carrier gas inlet and outlet openings and around the conduit for vaporizing a test specimen in the barrel and preventing condensation of the resulting vapor prior to delivery of the carrier gas and vapor mixture into the inlet end of the gas chromatographic column.

2. For use with a gas chromatograph, apparatus for generating a mixture of carrier gas and test specimen vapor for delivery into the gas chromatograph which comprises as an assembly:

a. a barrel open at one end to receive a specimen to be vaporized and having axially-spaced inlet and outlet openings to receive carrier gas and to discharge a mixture of carrier gas and specimen vapor, b. an elongated cylindrical probe slidable axially in close fitting engagement with the barrel having an elongated specimen chamber and axially-spaced carrier gas inlet and outlet openings for registry with the barrel carrier gas inlet and outlet openings for carrier gas flow axially through the specimen chamber.

c. barrel closure means secured to the open end of the barrel to close the barrel open end while carrier gas is flowing in contact with a test specimen in the barrel, and d. heating means comprising an electrical resistance heating coil disposed around the barrel between and extending between the barrel carrier gas inlet and outlet openings for raising a test specimen in the barrel to vaporization temperature while carrier vapor flows axially through the barrel from the barrel carrier gas inlet opening to the barrel carrier gas outlet opening.

3. The apparatus of claim 2 in which the barrel closure means comprises a compression fitting to seal gas tightly against the probe neck portion to prevent carrier gas escape during specimen vaporization intervals and against the probe shank portion to prevent air flow into the barrel or carrier gas loss through the open end of the barrel without restricting carrier gas flow from within the barrel to a point outside the barrel through the probe specimen chamber during test specimen loading operations.

4. The apparatus of claim 2 including a carrier gas supply line communicating with the carrier gas inlet opening of the barrel and a gas conduit connected to the barrel to receive carrier gas and specimen vapor mixtures issuing through the barrel gas outlet opening for delivery into a gas chromatographic column.

* * * * *